United States Patent
Paul et al.

(10) Patent No.: US 9,675,410 B2
(45) Date of Patent: Jun. 13, 2017

(54) FLEXIBLE POLYMER ELECTRODE FOR MRI-GUIDED POSITIONING AND RADIO FREQUENCY ABLATION

(75) Inventors: Saurav Paul, Minnetonka, MN (US); Troy T. Tegg, Elk River, MN (US); Chou Thao, Brooklyn Park, MN (US); Harry Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1057 days.

(21) Appl. No.: 11/966,576

(22) Filed: Dec. 28, 2007

(65) Prior Publication Data

US 2009/0171188 A1  Jul. 2, 2009

(51) Int. Cl.
| | |
|---|---|
| A61B 5/05 | (2006.01) |
| A61B 18/14 | (2006.01) |
| A61B 5/055 | (2006.01) |
| A61B 5/06 | (2006.01) |
| A61B 18/00 | (2006.01) |
| A61B 34/20 | (2016.01) |
| A61B 90/00 | (2016.01) |

(52) U.S. Cl.
CPC ......... *A61B 18/1492* (2013.01); *A61B 5/055* (2013.01); *A61B 5/06* (2013.01); *A61B 2018/00702* (2013.01); *A61B 2018/00791* (2013.01); *A61B 2018/00815* (2013.01); *A61B 2034/2068* (2016.02); *A61B 2090/374* (2016.02); *A61B 2090/3954* (2016.02)

(58) Field of Classification Search
USPC ............ 600/411, 422, 423; 607/2, 5, 6, 100, 607/101, 113, 116, 122, 127; 606/27, 32, 606/41
See application file for complete search history.

(56) References Cited

U.S. PATENT DOCUMENTS

| | | |
|---|---|---|
| 4,572,198 A | 2/1986 | Codrington |
| 5,143,090 A | 9/1992 | Dutcher |
| 5,271,400 A | 12/1993 | Dumoulin et al. |
| 5,307,808 A | 5/1994 | Dumoulin et al. |
| 5,318,025 A | 6/1994 | Dumoulin et al. |
| 5,391,199 A | 2/1995 | Ben-Haim |

(Continued)

FOREIGN PATENT DOCUMENTS

| | | |
|---|---|---|
| WO | 00/25672 | 5/2000 |
| WO | 2004/068947 A2 | 8/2004 |
| WO | 2004/113945 A2 | 12/2004 |

OTHER PUBLICATIONS

Zuehlsdorff et al. MR Coil Design for Simultaenous Tip Tracking and Curvature Delineation of a Catheter. Magnetic Resonance in Medicine. 52:214-218. 2004.*

(Continued)

*Primary Examiner* — James Kish
(74) *Attorney, Agent, or Firm* — Dykema Gossett PLLC

(57) ABSTRACT

An electrode for use on a medical device is disclosed. The electrode may have a main body of electrically conductive material extending along an axis and may have a proximal end and a distal end. The electrode may also include a magnetic resonance imaging (MRI) tracking coil disposed in the body. The MRI tracking coil may comprise electrically insulated wire. A catheter including an electrode, as well as a method for determining the location of an electrode, are also disclosed.

20 Claims, 2 Drawing Sheets

(56) References Cited

U.S. PATENT DOCUMENTS

| | | | |
|---|---|---|---|
| 5,443,489 A | 8/1995 | Ben-Haim |
| 5,715,822 A | 2/1998 | Watkins et al. |
| 5,769,843 A | 6/1998 | Abela et al. |
| 5,846,198 A | 12/1998 | Killmann |
| 5,868,674 A | 2/1999 | Glowinski et al. |
| 5,916,162 A | 6/1999 | Snelten |
| 5,938,603 A | 8/1999 | Ponzi |
| 5,954,665 A | 9/1999 | Ben-Haim |
| 6,016,439 A | 1/2000 | Acker |
| 6,171,240 B1 | 1/2001 | Young et al. |
| 6,185,448 B1 | 2/2001 | Borovsky |
| 6,226,432 B1 | 5/2001 | Gonda et al. |
| 6,226,543 B1 | 5/2001 | Gilboa et al. |
| 6,241,724 B1 | 6/2001 | Fleischman et al. |
| 6,246,896 B1 | 6/2001 | Dumoulin et al. |
| 6,275,721 B1 | 8/2001 | Darrow et al. |
| 6,289,233 B1 | 9/2001 | Dumoulin et al. |
| 6,377,048 B1 | 4/2002 | Golan et al. |
| 6,569,160 B1 | 5/2003 | Goldin et al. |
| 6,593,884 B1 | 7/2003 | Gilboa et al. |
| 6,600,319 B2 | 7/2003 | Golan |
| 6,642,297 B1 | 11/2003 | Hyatt |
| 6,701,176 B1 | 3/2004 | Halperin et al. |
| 6,704,594 B1 | 3/2004 | Blank et al. |
| 6,736,704 B2 | 5/2004 | Kennedy |
| 6,749,571 B2 | 6/2004 | Varghese |
| 6,862,468 B2 | 3/2005 | Smith |
| 6,904,307 B2 | 6/2005 | Karmarkar |
| 6,932,813 B2 | 8/2005 | Thompson et al. |
| 6,968,236 B2 | 11/2005 | Hagele |
| 7,048,716 B1 | 5/2006 | Kucharczyk |
| 7,155,271 B2 | 12/2006 | Halperin |
| 7,166,075 B2 | 1/2007 | Varghese |
| 7,250,049 B2 | 7/2007 | Roop et al. |
| 7,264,619 B2 | 9/2007 | Venturelli |
| 7,289,839 B2 | 10/2007 | Dimmer et al. |
| 2003/0028095 A1* | 2/2003 | Tulley et al. .................. 600/422 |
| 2003/0050557 A1 | 3/2003 | Susil |
| 2003/0208252 A1 | 11/2003 | O'Boyle |
| 2003/0236456 A1 | 12/2003 | Graham |
| 2004/0116800 A1 | 6/2004 | Helfer |
| 2004/0116801 A1 | 6/2004 | Konings |
| 2004/0220470 A1 | 11/2004 | Karmarkar et al. |
| 2004/0230114 A1 | 11/2004 | Clatterbaugh et al. |
| 2005/0014995 A1 | 1/2005 | Amundson |
| 2005/0054914 A1 | 3/2005 | Duerk et al. |
| 2005/0070972 A1 | 3/2005 | Wahlstrand |
| 2005/0102006 A1 | 5/2005 | Whitehurst |
| 2005/0171427 A1 | 8/2005 | Nevo et al. |
| 2005/0215886 A1 | 9/2005 | Schmidt |
| 2005/0215899 A1 | 9/2005 | Trahey et al. |
| 2005/0261569 A1 | 11/2005 | Schulz |
| 2005/0261571 A1 | 11/2005 | Willis |
| 2006/0030844 A1 | 2/2006 | Knight |
| 2006/0084861 A1 | 4/2006 | Blank et al. |
| 2006/0084866 A1 | 4/2006 | Lewkonya |
| 2006/0100506 A1 | 5/2006 | Halperin |
| 2006/0118319 A1 | 6/2006 | Wang |
| 2006/0135961 A1 | 6/2006 | Rosenman |
| 2006/0229659 A1 | 10/2006 | Gifford |
| 2007/0066972 A1* | 3/2007 | Ormsby et al. .................. 606/41 |
| 2007/0078457 A1 | 4/2007 | Paul et al. |
| 2007/0088244 A1 | 4/2007 | Millet |
| 2007/0088416 A1 | 4/2007 | Atalar |
| 2007/0100240 A1 | 5/2007 | Hiltawsky |
| 2007/0106148 A1 | 5/2007 | Dumoulin |
| 2007/0123764 A1 | 5/2007 | Thao et al. |
| 2007/0156205 A1 | 7/2007 | Larson et al. |
| 2007/0167705 A1 | 7/2007 | Chiang |
| 2007/0255132 A1 | 11/2007 | Shalgi |
| 2007/0282301 A1 | 12/2007 | Segalescu |
| 2007/0293754 A1 | 12/2007 | Schneid |
| 2008/0009700 A1 | 1/2008 | Dumoulin |
| 2008/0021308 A1 | 1/2008 | Dimmer |
| 2008/0033417 A1 | 2/2008 | Nields |
| 2008/0033418 A1 | 2/2008 | Nields |
| 2008/0033419 A1 | 2/2008 | Nields |
| 2008/0033420 A1 | 2/2008 | Nields |
| 2008/0038146 A1 | 2/2008 | Wachter |
| 2008/0045908 A1 | 2/2008 | Gould |

OTHER PUBLICATIONS

Alford, Superconducting Receive Coils for a Compact Low Field MRI System, http://ecce1.1sbu.ac.uk/research/pem/MRI.html.

Beals, New Brain-Imaging Technique Detects Early Stages of MCI, AD, Alzheimer's Association 2007 International Conference on Prevention of Dementia: Abstract P-231, presented Jun. 11, 2007.

Lederman, Cardiovascular Interventional MRI, Circulation, Nov. 8, 2005; 112(19):3009-3017.

Rutt, An Expandable Intravenous RF Coil for Arterial Wall Imaging, Journal of Magnetic Resonance Imaging, 8:226-234, 1998, http://www.imaging.robarts.ca/~brutt/Research/arterial.html.

Wacker et al., The Catheter-Driven MRI Scanner: A New Approach to Intravascular Catheter Tracking and Imaging—Parameter Adjustment for Interventional MRI, American Journal of Roentgenology: 183, Aug. 2004.

Weaver et al., Magnetic Resonance Elastography Using 3D Gradient Echo Measurements of Steady-State Motion, Medical Physics, vol. 28, No. 8, Aug. 2001.

Emerging Device Technology: MRI Coils, University of Birmingham, http://www.edt.bham.ac.uk/mri.htm.

Magnetic Resonance Elastography; http://india.cchem.berkeley.edu/~vdemas/Elastography.htm.

MR Elastography Quantitatively Assesses Liver Fibrosis, Reuters Health Information 2006; Radiology 2006; 240:440-448, http://www.medscape.com/viewarticle/544969.

The Walsworth Group (Harvard-Smithsonian Center for Astrophysics; Harvard University Department of Physics), Photos of the Week from 2006, Dec. 19, 2006, www.cfa.harvard.edu/Walsworth/Activities/Photo_of_Week2006.html.

International Search Report and Written Opinion in PCT/US2008/084203 mailed Feb. 4, 2009.

U.S. Appl. No. 11/964,194, filed Dec. 26, 2007 for Catheter Electrode That Can Simultaneously Emit Electrical Energy and Facilitate Visualization by Magnetic Resonance Imaging.

* cited by examiner

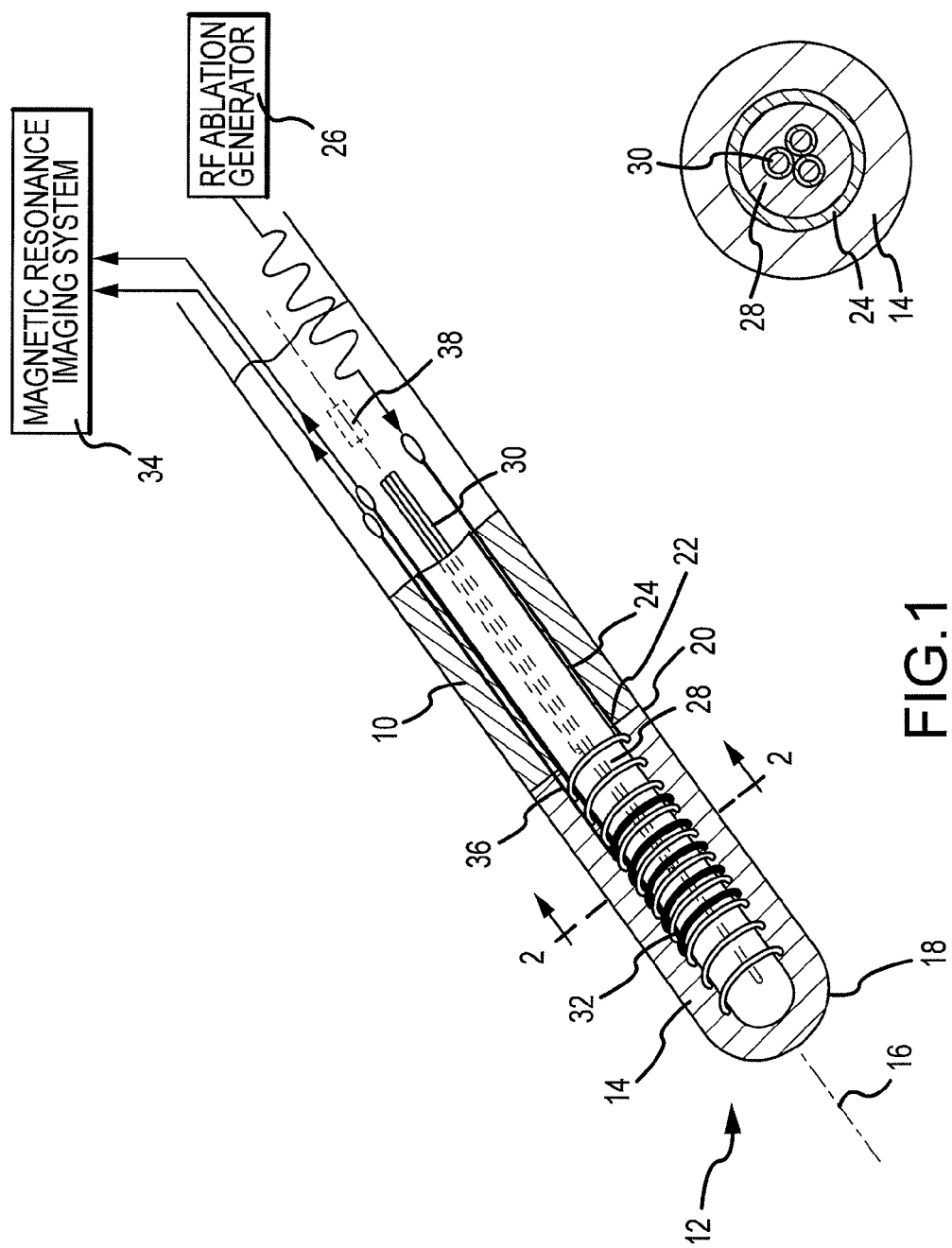

FLEXIBLE POLYMER ELECTRODE FOR MRI-GUIDED POSITIONING AND RADIO FREQUENCY ABLATION

BACKGROUND OF THE INVENTION a. Field of the Invention

The instant invention is directed toward a flexible polymer electrode, including a flexible polymer electrode for MRI-guided positioning and RF ablation.

b. Background Art

Catheters have been in use for medical procedures for many years. Catheters can be used for medical procedures to examine, diagnose, and treat while positioned at a specific location within a body that is otherwise inaccessible without more invasive procedures. During these procedures a catheter is commonly inserted into a vessel near the surface of the body and is guided to a specific location within the body for examination, diagnosis, and/or treatment. For example, one procedure often referred to as "catheter ablation" utilizes a catheter to convey an electrical stimulus to a selected location within the human body to create tissue necrosis. Another procedure often referred to as "mapping" utilizes a catheter with sensing electrodes to monitor various forms of electrical activity in the human body.

Catheters are also used for medical procedures involving the human heart. Typically, the catheter is inserted in an artery or vein in the leg, neck, or arm of the patient and directed, sometimes with the aid of a guide wire or introducer, through the vessels until a distal tip of the catheter reaches the desired location for the medical procedure in the heart.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes. Mapping catheters also often contain a plurality of sensing electrodes to monitor various forms of electrical activity in the human body.

An application may be utilized to create images of the catheter's surroundings. Images may be acquired through visible light, ultrasound, or magnetic resonance (MR). The application may be used to acquire high resolution radiographic images of tissue surrounding the catheter, for example, the acquisition of high resolution magnetic resonance images of blood vessel walls for the visualization and differentiation of various types of tissues and plaques.

Magnetic resonance imaging (MRI) may also be employed during a medical procedure to assist a physician in guiding a catheter and/or a portion of a catheter, such as an electrode. For example, tracking devices may be attached to a catheter (or other medical device) to be tracked. The tracking device may comprise a coil (e.g., induction coil). An MR pulse sequence may be performed using the coil to acquire a signal which indicates the location of the tracked device (e.g., catheter). The location of the coil may be determined and superimposed at the corresponding location in a medical image acquired with an MR imaging system.

Conventional designs for catheters for MRI-guided electrode positioning may rely on a plurality of tracking devices placed at discrete locations along the longitudinal axis of the catheter shaft. The tracking devices may be located on the shaft proximal to an electrode. The tracking devices may be utilized to sense and indicate the location and orientation of the catheter within a body through a control system. The control system may also be used to control a set of imaging coils to image selective areas of the body cavity and/or to control the amount of energy applied to electrodes (e.g., ablation elements) on the catheter to treat target tissue. The energy may cause heating, and at certain temperatures, tissue cells may be destroyed. The tracking devices may be used to compute the curve of the shaft as an interpolated polynomial, such as a cubic spline. The computed curve may then be extrapolated to estimate the projected location of the electrode at the distal end of the catheter shaft. The location of the electrode at the distal end of the catheter shaft may thus be an indirectly computed estimate, not a directly measured value. Further, it may be desirable for an electrode to conform to the tissue surface that has been targeted for treatment. For example, the electrode may undergo deflection or deformation when the electrode comes into physical contact with the tissue. Any deflection or deformation of the electrode may not be estimated by extrapolating from the shape of the catheter shaft. Accordingly, an electrode that conforms to the tissue surface as desired may complicate and/or render useless the extrapolation method.

Thus, there remains a need for a system and method for directly measuring the location of an electrode disposed on a catheter (e.g., the electrode disposed at the distal tip of a catheter) without having to resort to extrapolation or estimation.

BRIEF SUMMARY OF THE INVENTION

It is desirable to provide an electrode that may be configured for compatibility with MR imaging applications, while retaining the electrical, thermal, and mechanical properties of conventional electrodes.

An electrode for use on a medical device is disclosed. The electrode may have a main body of electrically conductive material extending along an axis and may have a proximal end and a distal end. The electrode may also include a magnetic resonance imaging (MRI) tracking coil disposed in the body. The MRI tracking coil may comprise electrically insulated wire, for example. In a preferred embodiment, at least a portion of the body may comprise a flexible, polymer material.

A catheter including the electrode is also disclosed. The catheter may include a shaft and an electrode disposed on the shaft. The electrode may have a main body of electrically conductive material extending along an axis and may have a proximal end and a distal end. The electrode may also include a magnetic resonance imaging (MRI) tracking coil disposed in the body. The MRI tracking coil may comprise electrically insulated wire, for example.

A method for determining the location of an electrode is also disclosed. The method may include the step of providing an electrode having a main body extending along an axis and having a proximal end and a distal end. The method may further include the step of disposing a magnetic resonance imaging (MRI) tracking coil in the body. The MRI tracking coil may comprise electrically insulated wire. The method may further include the steps of transmitting a signal from the MRI tracking coil to a magnetic resonance imaging (MRI) system and depicting the location of the electrode.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is a longitudinal, cross-sectional view of a catheter shaft including an electrode in accordance with an embodiment of the invention.

FIG. 2 is a radial, cross-sectional view of an electrode in accordance with an embodiment of the invention.

DETAILED DESCRIPTION OF THE INVENTION

Figure 3:
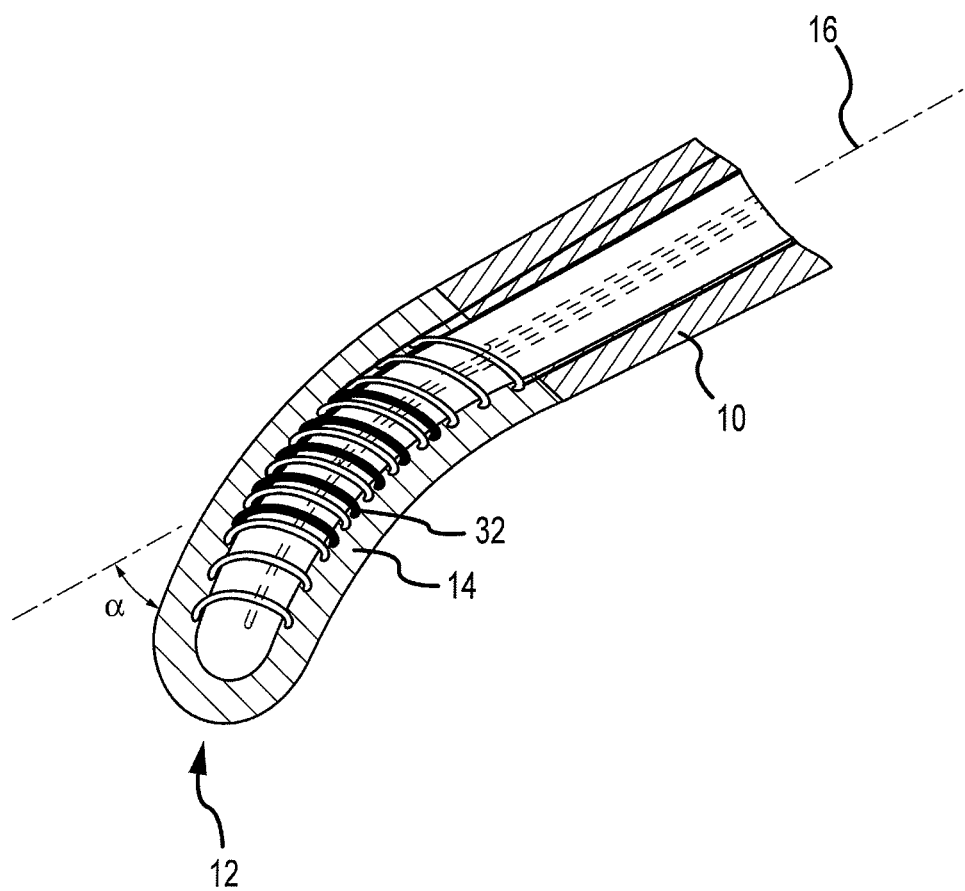
FIG. 3 is a longitudinal, sectional view of a catheter shaft including an electrode showing a deflected electrode in accordance with an embodiment of the invention.

FIG. 1 illustrates a longitudinal, cross-sectional view of a catheter shaft 10 including an electrode 12 in accordance with an embodiment of the invention. Shaft 10 may be designed for insertion into a main lumen of a sheath for eventual insertion into the body of a patient. Shaft 10 may comprise one or a plurality of layers. For example and without limitation, shaft 10 may comprise a braided layer of metal fibers for additional stability and one or more layers of polymeric materials to create the desired stiffness and/or flexibility for the catheter. Shaft 10 may define one or more lumens for electrical leads, steering wires, or various other items that may be utilized within shaft 10. Shaft 10 may include a proximal section and a distal section. As used herein, "proximal" generally refers to a direction away from the body of a patient and toward a clinician. In contrast, "distal" generally refers to a direction toward the body of the patient and away from the clinician. While electrode 12 may be disclosed and described in connection with a catheter, the use of a catheter is for illustration purposes only, and electrode 12 may also be utilized in connection with other medical devices.

Electrode 12 may be mechanically connected (e.g., attached) to the distal section of shaft 10. Although electrode 12 is described as connected to the distal section of shaft 10, an electrode 12 may be connected to one or more other locations along shaft 10 in other embodiments. Electrode 12 may be utilized for radio frequency (RF) ablation and may have the electrical, thermal, and mechanical properties required of an electrode used for RF ablation. For example, at least a portion of electrode 12 may comprise an electrically conductive material. In an embodiment, electrode 12 may comprise a main body 14 extending along an axis 16. Body 14 of electrode 12 may have a distal end 18 and a proximal end 20. Body 14 of electrode 12 may be generally cylindrical in shape. Although a cylindrical shape is described and illustrated, electrode 12 may be formed in other shapes. Distal end 18 may include a rounded tip. Distal end 18 may be rounded so as to minimize irritation to the body cavity into which a medical device including the electrode 12 may be inserted. Body 14 of electrode 12 may include a lumen in an embodiment. The lumen may be porous or non-porous. The lumen may extend along axis 16 of body 14 and may be open at both ends. In another embodiment, the lumen may be a blind bore 22 with a closed end and an open end. Blind bore 22 may have a circular sidewall extending from a floor thereof (e.g., the closed end) and may open toward the proximal end 20 of body 14.

At least a portion of electrode 12 may be generally flexible in an embodiment. For example, at least a portion of electrode 12 may be configured to conform to the tissue surface targeted for treatment, and may therefore, deflect and/or undergo deformation when electrode 12 comes into physical contact with tissue. Body 14 of electrode 12 may comprise a polymer material in an embodiment. In particular, body 14 may comprise an electrically conductive polymer. The polymer may comprise a silicone material, for example. Body 14 may have electrically conductive particles dispersed therein at a predefined density. The density of the electrically conductive particles may be defined to achieve a desired electrical conductivity. The electrically conductive particles may comprise metal particles in an embodiment. For example and without limitation, the electrically conductive particles may comprise a metal such as gold, silver, platinum, iridium, titanium, tungsten, or a combination thereof. The electrically conductive particles may be non-magnetically responsive. In an embodiment, the electrically conductive particles may have magnetic susceptibility less than $1 \times 10^{-4}$. Magnetic susceptibility may refer to the degree of magnetization of a material (e.g., the extent that the material is affected by a magnetic field) in response to a magnetic field.

As described above, electrode 12 may be configured for imparting energy (e.g., RF energy) to target tissue. An electrical conductor 24 may be configured to carry ablative energy (e.g. RF current) from an energy source in a controller (not shown) to electrode 12. Electrical conductor 24 may have a first end coupled to body 14 of electrode 12. Electrical conductor 24 may have a second end configured for connection to an energy source 26. Energy source 26 may comprise a radio frequency ablation generator in an embodiment. Electrical conductor 24 may extend within shaft 10 along axis 14. Electrical conductor 24 may comprise an electrically conductive wire. For example, and without limitation, electrical conductor 24 may comprise copper wire. Electrical conductor 24 may have an uninsulated portion for electrical contact with electrode 12. For example, the first end (e.g., a distal end) of electrical conductor 24 may be uninsulated. At least a portion of the remainder of electrical conductor 24 may be electrically insulated. For example, the portion of electrical conductor 24 extending along shaft 10 outside of electrode 12 may be electrically insulated.

In an embodiment, the uninsulated portion of electrical conductor 24 may be electrically connected to electrode 12 at a point connection. For example, electrical conductor 24 may have a first end that is electrically coupled to proximal end 20 of body 14 at a single point. In a preferred embodiment, at least part of the uninsulated portion of electrical conductor 24 may be formed in a plurality of turns, as illustrated in FIGS. 1-3. Electrical conductor 24 may be formed (e.g., wound) into a substantially cylindrical shape and may have a longitudinal axis that is coincident with axis 14 of electrode 12. The plurality of turns of electrical conductor 24 may be disposed in the lumen or blind bore 22 and may be configured to engage the circular sidewall of blind bore 22 in an embodiment. The shape of electrical conductor 24 in this embodiment may be formed so as to more evenly distribute the energy from RF ablation generator 26 throughout electrode 12. In particular, the shape of electrical conductor 24 (e.g., wound in a plurality of turns and extending axially throughout the depth of the blind bore 22) allows conduction from the coiled conductor 24 substantially radially through electrode 12, as opposed to a more axial path of conduction along axis 14 of electrode 12 if the conductor 24 is connected to a point on the proximal end 20 of electrode 12. Furthermore, the shape of electrical conductor 24 may provide some mechanical integrity to the electrical connection between conductor 24 and the electrode 12

In other embodiments, the uninsulated portion of electrical conductor 24 (e.g., the first end of electrical conductor 24 nearest to the electrode 12) may be electrically connected to one of a screen, a mesh, a braid, or a fabric of electrically conductive material. The screen, mesh, braid, or fabric may engage body 14 (e.g., the sidewall of blind bore 22 in an embodiment) and may also be utilized to distribute the energy from RF ablation generator 26 throughout electrode 12 in the same manner as the coiled conductor 24.

Referring now to FIG. 2, which illustrates a cross-sectional view of electrode 12 in accordance with an embodiment of the invention, a portion 28 of shaft 10 may be disposed in body 14 (e.g., blind bore 22 in an embodiment) as well. Portion 28 may have a longitudinal axis that is coincident with axis 16 of body 14. In the embodiment where electrical conductor 24 is coiled, conductor 24 may be wound in a substantially circular cross-sectional shape and may be disposed so as to encircle portion 28 (as illustrated). Portion 28 may be electrically insulative in an embodiment. Portion 28 may also be thermally conductive in an embodiment. A thermal sensor 30 may extend within at least the distal end of catheter shaft 12 and within electrode 12 along axis 16. In particular, thermal sensor 30 may extend within thermally conductive portion 28 of shaft 10 in an embodiment. Thermal sensor 30 may be located along a centerline of the electrode 12 in an embodiment. Thermal sensor 30 may be located at or near the distal end 18 of electrode 12 (e.g., the tip) in an embodiment. Thermal sensor 30 may thus be in close proximity to the electrode/tissue interface when the electrode is oriented so that the tip of the electrode 12 contacts tissue during ablation, which may be advantageous in some embodiments. For example and without limitation, thermal sensor 30 may comprise a thermocouple. Thermal sensor 30 may be operatively connected to a controller and may be configured to provide temperature feedback during ablation to avoid clotting and/or blood boiling, for example, which may occur if electrode 12 (and hence by extension the subject tissue) reaches an excessive temperature.

Electrode 12 may be configured for compatibility with MRI-guided applications. Accordingly, electrode 12 may include a magnetic resonance imaging (MRI) tracking coil 32. MRI tracking coil 32 may be wound in a substantially cylindrical shape and may have a longitudinal axis that is coincident with axis 16 of body 14. MRI tracking coil 32 may be disposed in body 14 of electrode 12. For example, MRI tracking coil 32 may be embedded within body 14 of electrode 12. In another example, MRI tracking coil 32 may be disposed in a lumen, for example and without limitation, blind bore 22. MRI tracking coil 32 may be disposed so as to encircle portion 28 of shaft 10 and may or may not contact the circular sidewall of blind bore 22 in this example. MRI tracking coil 32 may comprise an electrically insulated wire capable of carrying the current required to create a coil signal. MRI tracking coil 32 may function as an RF antenna typically used in interventional MRI applications, and accordingly will be formed having a predetermined number of turns to ensure adequate performance, in view of the various other portions of the MRI system with which it will be required to interact. In this regard, an MR pulse sequence may be performed using MRI tracking coil 32 to acquire a signal that may be indicative of a position or a location of electrode 12. For example, an electromagnetic force (EMF) may be induced in the MRI tracking coil 32 as would be understood by one of ordinary skill in the art. The signal (e.g., EMF) may be transmitted to a magnetic resonance imaging (MRI) system 34. The MRI system 34 may be responsive to the signal from MRI tracking coil 32 to depict a location of electrode 12 in a patient. For example, MRI system 34 may utilize the EMF to render a graphic display of the position or location of electrode 12. The MRI system 34 may also be configured to acquire image data from a patient (equipment for this function not shown), and to display an overall image reconstructed using the acquired image data and the acquired position-indicative data (i.e., from the induced EMF signal from the MRI tracking coil 32), which may depict the location of electrode 12 in a patient. In an embodiment, another electrical conductor 36 may carry the signal (e.g., EMF) from MRI tracking coil 32 to MRI system 34. Electrical conductor 36 may extend within catheter shaft 12 along axis 14 of electrode 12.

As described above, in a preferred embodiment, at least a portion of body 14 of electrode 12 may be generally flexible and may be configured for deformation and/or deflection in a number of directions relative to axis 16 of body 14. For example, a distal portion of body 14 may be generally flexible. Referring to FIG. 3, the body is shown in a deflected and/or deformed position, designated by reference number 14$_{deflected}$, and is shown deflected at an angle α relative to axis 14. Although this particular deflection is illustrated, body 14 may be deflected and/or deformed in various other ways, including in a direction along different axes other than the axis of the shaft 10. The deflection and/or deformation of electrode 12 may not be able to be estimated merely by extrapolating the shape of a catheter shaft that holds a rigid and/or solid electrode at its distal end. Accordingly, it may be difficult to estimate a projected location of a flexible electrode at the distal end of a catheter shaft without a direct measurement.

In an embodiment, MRI tracking coil 32 may be configured to move in correspondence with deflection of body 14. Referring again to FIG. 3, MRI tracking coil 32$_{deflected}$ is shown in a new position, away from its original position, where the tip of electrode 12 is deflected. Accordingly, MRI tracking coil 32$_{deflected}$ may be configured to track the deformation and/or deflection of electrode 12 through a direct measurement. MRI tracking coil 32 may thus be configured to provide direct localization of electrode 12 as electrode 12 conforms to the target tissue surfaces and may allow for direct measurement of the location of electrode 12. In prior art embodiments, one or more MRI tracking coils 38 may be disposed along shaft 10, as opposed to electrode 12. Accordingly, the exact location of electrode 12 may only be extrapolated based on a curve computed using the data obtained from the prior art MRI tracking coils 38 on shaft 10. Prior art MRI tracking coils 38 do not provide direct measurement of the position or location of electrode 12.

A method for determining the location of an electrode 12 is also disclosed. The method may include the step of providing an electrode 12 having a main body 14 of electrically conductive material extending along an axis 16 and having a distal end 18 and a proximal end 20. The method may also include the step of disposing an MRI tracking coil 32 in body 14. MRI tracking coil 32 may comprise electrically insulated wire. The method may also include the step of transmitting a signal from MRI tracking coil 32 to an MRI system 34 (e.g., through electrical conductor 36) and depicting a location of electrode 12. Image data may also be obtained from a patient using MRI system 34 and an imaging (e.g., receive) coil disposed on shaft 10, for example. MRI system 34 may also use this image data in displaying an image depicting the location of electrode 12. In some embodiments, the method may include the steps of deflecting at least a distal portion of body 14 of electrode 12 relative to axis 14. MRI tracking coil 32 may be configured to move in correspondence with the deflection of body 14. Accordingly, MRI tracking coil 32 may also move to a new position, away from its original position, when the tip of electrode 12 is deflected.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode for use on a medical device comprising:
a main body of electrically conductive material extending along an axis and comprising a proximal end, a distal end, and a wall disposed about and defining a lumen extending along said axis;
an electrical conductor having a first end coupled to said body and a second end configured for connection to an energy source, wherein said conductor comprises electrically conductive wire having an insulated portion and an uninsulated portion, the uninsulated portion formed in a plurality of turns, wherein said uninsulated portion of said electrically conductive wire is disposed in said lumen and wherein at least part of said uninsulated portion of said electrically conductive wire is configured to engage said wall; and
a magnetic resonance imaging (MRI) tracking coil comprising electrically insulated wire that is wound in a plurality of turns that each extend circumferentially around said axis, wherein said MRI tracking coil further comprises an opening configured to receive a portion of the medical device that extends along said axis, wherein said MRI tracking coil is one of:
embedded directly within said wall; and
disposed directly within said lumen,
further wherein said MRI tracking coil is electrically coupled with two wires that are configured to transmit an induced electromotive force to an MRI system when the MRI system is activated, said induced electromotive force being indicative of a location of said MRI tracking coil.

2. The electrode of claim 1, wherein said lumen comprises a blind bore opening toward said proximal end of said body.

3. The electrode of claim 1, wherein said body comprises a polymer.

4. The electrode of claim 3, wherein said body comprises electrically conductive particles dispersed therein at a predefined density.

5. The electrode of claim 4, wherein said particles comprise a material with a magnetic susceptibility less than about $1 \times 10^{-4}$.

6. The electrode of claim 1, further comprising a thermal sensor disposed within a portion of said medical device that is disposed in said lumen, wherein said portion of said medical device is electrically insulative and thermally conductive.

7. The electrode of claim 1, wherein at least a distal portion of said body is configured for deflection relative to said axis.

8. The electrode of claim 7, wherein said MRI tracking coil is configured to move in correspondence with said deflection of said distal portion of said body.

9. An electrode for use on a medical device comprising:
a main body of electrically conductive material extending along an axis and comprising a proximal end, a distal end, and a wall disposed about and defining a lumen extending along said axis;
an electrical conductor having a first conductor end and a second conductor end configured for connection to an energy source, said first conductor end electrically connected to one of a screen, a mesh, a braid, or a fabric of electrically conductive material engaging said body, wherein one of said screen, said mesh, said braid, or said fabric of electrically conductive material is disposed in said lumen and wherein at least part of one of said screen, said mesh, said braid, or said fabric of electrically conductive material is configured to engage said wall; and
a magnetic resonance imaging (MRI) tracking coil comprising electrically insulated wire that is wound in a plurality of turns that each extend circumferentially around said axis, wherein said MRI tracking coil further comprises an opening configured to receive a portion of the medical device that extends along said axis, wherein said MRI tracking coil is one of:
embedded directly within said wall; and
disposed directly within said lumen,
further wherein said MRI tracking coil is electrically coupled with two wires that are configured to transmit an induced electromotive force to an MRI system when the MRI system is activated, said induced electromotive force being indicative of a location of said MRI tracking coil.

10. The electrode of claim 9, wherein said lumen comprises a blind bore opening toward said proximal end of said body.

11. The electrode of claim 9, wherein said body comprises a polymer.

12. The electrode of claim 11, wherein said body comprises electrically conductive particles dispersed therein at a predefined density.

13. The electrode of claim 12, wherein said particles comprise a material with a magnetic susceptibility less than about $1 \times 10^{-4}$.

14. The electrode of claim 9, further comprising a thermal sensor disposed within a portion of said medical device that is disposed in said lumen, wherein said portion of said medical device is electrically insulative and thermally conductive.

15. The electrode of claim 9, wherein at least a distal portion of said body is configured for deflection relative to said axis.

16. The electrode of claim 15, wherein said MRI tracking coil is configured to move in correspondence with said deflection of said distal portion of said body.

17. An electrode for use on a medical device comprising:
a main body of electrically conductive material extending along an axis and comprising a proximal end, a distal end, and a wall disposed about and defining a lumen extending along said axis;
an electrical conductor having a first end electrically connected to one of a screen, a mesh, a braid, or a fabric of electrically conductive material engaging said body, and a second end configured for connection to an energy source, wherein said conductor comprises electrically conductive wire having an insulated portion and an uninsulated portion, the uninsulated portion formed in a plurality of turns, wherein one of said screen, said mesh, said braid, or said fabric of electrically conductive material is disposed in said lumen, wherein at least part of one of said screen, said mesh, said braid, or said fabric of electrically conductive material is configured to engage said wall, wherein said uninsulated portion of said electrically conductive wire is disposed in said lumen, and wherein at least part of said uninsulated portion of said electrically conductive wire is configured to engage said screen, said mesh, said braid, or said fabric of electrically conductive material; and a magnetic resonance imaging (MRI) tracking coil comprising electrically insulated wire that is wound in a plurality of turns that each extend circumferentially around said axis, wherein said MRI tracking coil further comprises an opening configured to receive a portion of the medical device that extends along said axis, wherein said MRI tracking coil is one of:

embedded directly within said wall; and disposed directly within said lumen, further wherein said MRI tracking coil is electrically coupled with two wires that are configured to transmit an induced electromotive force to an MRI system when the MRI system is activated, said induced electromotive force being indicative of a location of said MRI tracking coil.

18. The electrode of claim 17, wherein said lumen comprises a blind bore opening toward said proximal end of said body.

19. The electrode of claim 17, wherein at least a distal portion of said body is configured for deflection relative to said axis.

20. The electrode of claim 19, wherein said MRI tracking coil is configured to move in correspondence with said deflection of said distal portion of said body.

* * * * *